United States Patent [19]
Sutter

[11] Patent Number: 5,746,739
[45] Date of Patent: May 5, 1998

[54] BIPOLAR COAGULATION FORCEPS WITH RINSING TUBE

[75] Inventor: Hermann Sutter, Gundelfingen, Germany

[73] Assignee: Select Medizin-Technik Hermann Sutter GmbH, Freiburg, Germany

[21] Appl. No.: 554,330

[22] Filed: Nov. 6, 1995

[30] Foreign Application Priority Data

Nov. 10, 1994 [DE] Germany .............. 44 40 158.2
Nov. 10, 1994 [DE] Germany .............. 9418006 U

[51] Int. Cl.⁶ ................................. A61B 17/39
[52] U.S. Cl. ..................... 606/51; 606/50; 606/52
[58] Field of Search ................... 606/32, 41, 49, 606/50–52

[56] References Cited

U.S. PATENT DOCUMENTS

| | | | |
|---|---|---|---|
| 4,041,952 | 8/1977 | Morrison, Jr. et al. | 606/52 |
| 4,096,864 | 6/1978 | Kletschka et al. | |
| 4,567,890 | 2/1986 | Ohta et al. | 606/51 |
| 5,209,747 | 5/1993 | Knoepfler | 606/52 |
| 5,464,405 | 11/1995 | Fujitsu et al. | 606/51 |

FOREIGN PATENT DOCUMENTS 31 10 666 C2  8/1984  Germany.

*Primary Examiner*—Jennifer Bahr
*Assistant Examiner*—Rosiland Kearney
*Attorney, Agent, or Firm*—Panitch Schwarze Jacobs & Nadel, P.C.

[57] ABSTRACT

A bipolar coagulation forceps 1 with a connection 2 for high frequency energy and two forceps limbs 4 capable of being pressed together against a spring tension is so constructed that a rinsing tube can be provided in a simple manner and without impinging on the space between the forceps limbs 4. For this purpose, the forceps limbs 4 comprise grips 5 which can be pushed together against spring tension with working limbs 6 subsequently fastened on them, whereby then at least one of the working limbs 6 has a hollow cross section or is constructed as a tube and has a connection 7 for the rinsing fluid, so that guidance parts 11 can be arranged between the grips 5 for the reciprocal guidance of the working tips 3 of the forceps 1. The working limbs 6 are for this reason arranged on parallel narrow sides 8 of the grips 5, that is lateral to the grip areas, where the guiding parts 11 are accommodated.

12 Claims, 2 Drawing Sheets

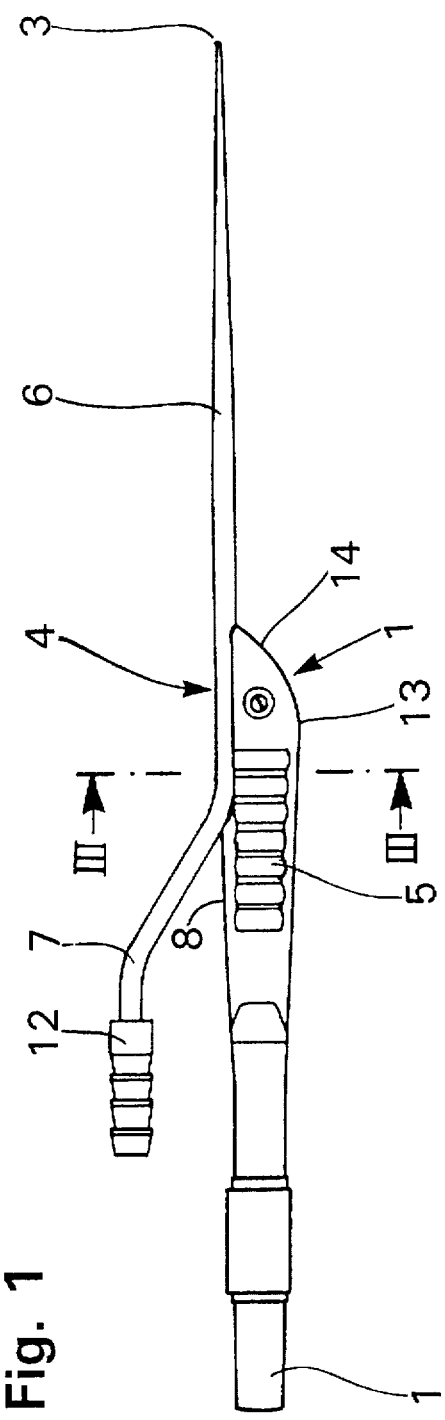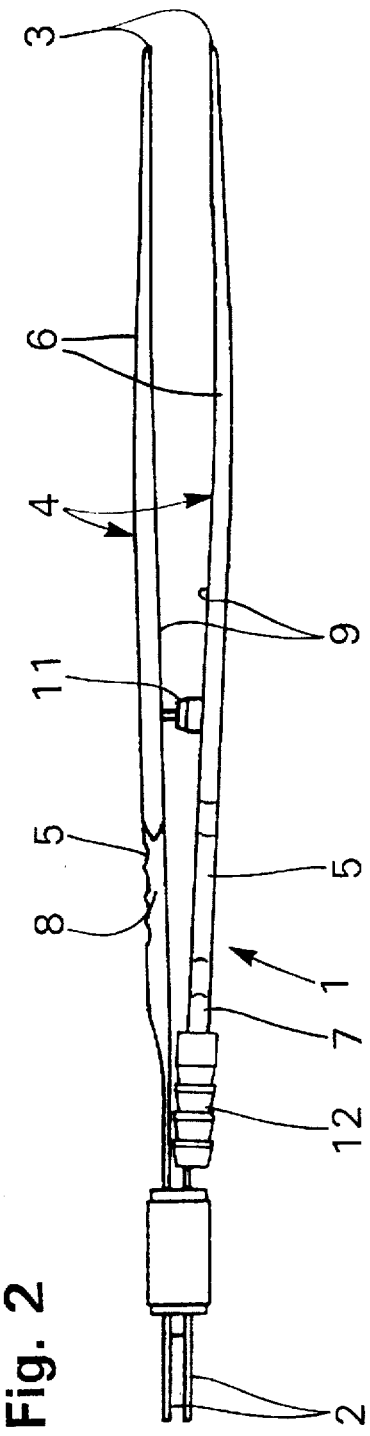

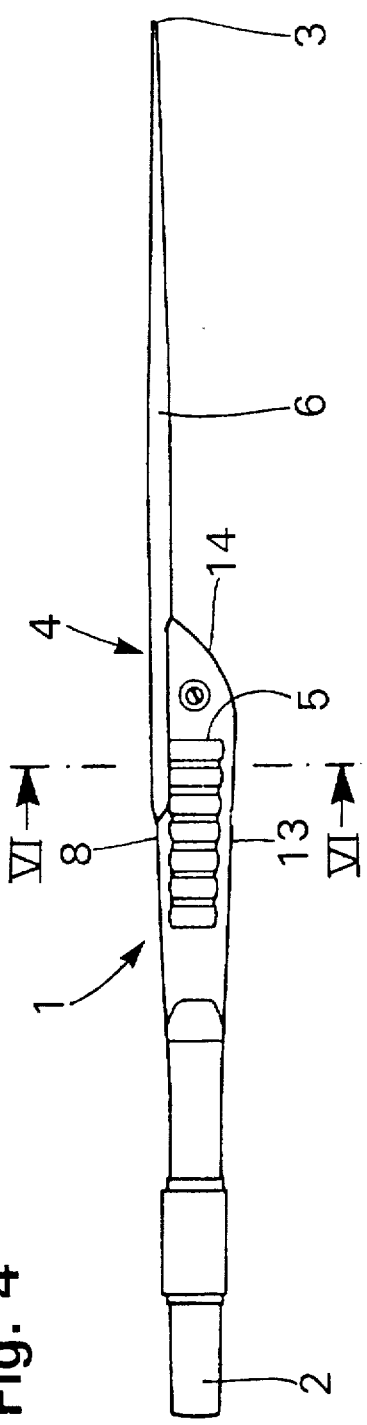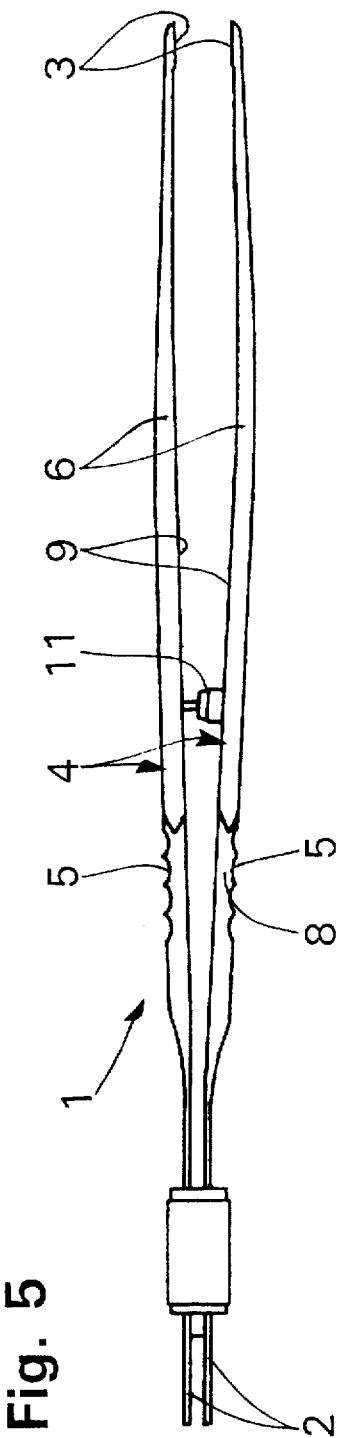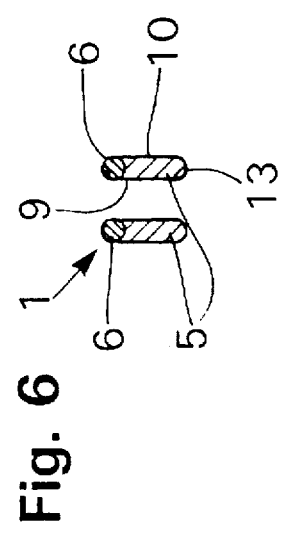

BIPOLAR COAGULATION FORCEPS WITH RINSING TUBE

FIELD OF THE INVENTION

The invention concerns a bipolar coagulation forceps with a connection for high frequency energy and with two forceps limbs which can be pressed together against spring tension, whose tips opposite the connection for high frequency energy form the poles for coagulation, whereby at least one forceps limb has a rinsing tube.

BACKGROUND OF THE INVENTION

Bipolar coagulation has been known for a long time, and a forceps for bipolar coagulation is known from DE 31 10 666 C2, but this does not have a rinsing tube.

High frequency current applied in a bipolar manner has fewer dangers and disadvantages for the patient in comparison with monopolar high frequency current. Of course, during coagulation in dry tissue, tissue parts can stick to the electrodes formed by the forceps limbs, and a previously coagulated vessel can be torn open upon removal of the forceps. If on the other hand coagulation is taking place in a hematoma, the tips can be covered with coagulated blood so that an insulation layer arises and further coagulation is hindered or prevented. In both cases, the coagulation forceps must be cleaned or be replaced by a new, clean instrument.

Rinsing with a saline solution can provide assistance in connection with dry tissue. In the case of a hematoma, the blood can be washed away by rinsing, the bleeding vessel exposed and coagulated before formation of a new hematoma.

There are known coagulation forceps of the type discussed at the beginning in which a continuous tube is welded to the inner surface of a forceps limb, through which rinsing fluid can be conveyed to the working tip. Such coagulation forceps have no special guidance of their working tips so that they can easily slip one over the other during the closing and coagulation procedure.

The guidance on the inner surfaces of the forceps limb known from DE 31 10 666 C2 is not compatible with a rinsing tube mounted on the inner surface of a forceps limb.

SUMMARY OF THE INVENTION

For this reason, there exists the object of creating a bipolar coagulation forceps of the type mentioned at the beginning, in which a rinsing tube is present, but nonetheless space for guidance parts is available on the forceps limbs, so that a secure guidance of the forceps limb and furthermore a rinsing in the area of the working tips is possible.

The solution for this seemingly contradictory object resides in the forceps limbs comprising grips which can be pressed together against springs with working limbs being subsequently fixed thereon, at least one working limb having a hollow cross section or being constructed as a tube, this hollow working limb having a connection for rinsing fluid and/or for a suction source, and the working limbs being arranged on parallel narrow sides of the grips.

Since at least one of the working limbs itself is constructed as a rinsing tube, there is no rinsing tube mounted on the inner side of the forceps limb. Consequently, no place is required for it on the inner side of the forceps limb.

For this reason, it is possible for contact and guidance parts to be mounted between the grips on the inner sides of these grips facing each other, at a distance from the narrow side bearing the working limbs, for restriction and/or guidance of the closing pathway of the working tips of the working limbs. The bipolar coagulation forceps thus advantageously have very good control chiefly in the grip area where the user applies the appropriate force so that the often very fine working tips can be moved toward each other with precision. Nonetheless, rinsing and/or sucking is possible in the working tip area. Mounting the working limbs belonging to the forceps on parallel narrow sides of the grips is also thereby advantageous, because these working limbs thereby further enlarge to a certain extent the width of the grips to be grasped for pressing together, and the user can see very well over these working limbs the spot to be worked upon. The control means can be provided trouble free on the inner side of the grip, because the actual working limbs are located, laterally of this area on the narrow sides which form the transition between the inner and the outer sides of the grips.

The cross section of the working limb can be round, especially circular. Their manufacture is consequently very simple, so that the production of the entire coagulation forceps can also be simplified. This is already simplified for the reason that identical grips and high frequency connections can be used for various coagulation forceps with which in any given case the working limbs are different, either in their length or even in their configuration.

The narrow sides of the grips can have a groove-like notch, especially a milling, with an angular or curved cross section, extending at least along the length over which the working limbs reach, whereby the curvature of the cross section of the groove-like notch corresponds to the curvature on the outer surface of the working limb or exceeds this somewhat. The grips on their narrow side can consequently somewhat embrace the working limbs and in addition also accommodate solder, if the working limbs are soldered to the grips.

It is advantageous in this regard if the working limbs extend over only one part of the longitudinal extent of the grips, preferably over approximately a third of the length of the grips, leaving free the remaining longitudinal areas lying nearer to the high frequency energy connection.

Consequently, a good spring action of the grips connected to each other is possible, undisturbed by the working limbs, and in addition, unnecessary material for a longer overlapping between working limb and grip is avoided.

There results above and beyond this the advantage that in the extension of the hollow working limb at its end facing away from the working tip on the narrow side of the grip, the rinsing and/or suction connection can be fastened, e.g. soldered or welded on, or be constructed in one piece as a continuation of the working limb. In order then to be able to fasten an appropriate hose or the like, without this disturbing the user, the rinsing connection can be bent away from the narrow side of the grip bearing the working limb in the plane of this grip which lies at a right angle to the closing movement. Therefore, the projection of the rinsing connection always lies just above the narrow side of the grip, but the rinsing connection itself is spaced from the grip owing to the bending away.

The thickness of the grip can approximately correspond to the diameter of the cross section of the working limb and the outer side as well of the inner side of each grip can be largely flush with the working limb borne by it. Consequently, even in the region of the grips, the forceps limbs can be brought close to each other, to the extent that it is already possible on the basis of the dimensions of the grip alone, without being impeded by the rinsing tube which is located in at least one of the working limbs. The inner sides and outer sides surface of the grip in question thus pass to a certain extent tangentially into the corresponding areas of the working limbs.

It should also be mentioned that the grips can carry working limbs with and/or without rinsing connection, or with solid cross section. This means that on one of such coagulation forceps both working limbs can also have in any given case a hollow cross section and a rinsing and/or suction connection. In like manner, however, the production engineering advantages also become effective if a coagulation forceps is manufactured in one case or another without rinsing connection, whereby then again the same grips with control means and high frequency energy connection, which can be moved toward each other against spring tension, can be used, so that corresponding rationalization advantages emerge in connection with the manufacture of bipolar coagulation forceps with and without rinsing connections.

The upper narrow side of the grips bearing the working limbs can be longer than the lower narrow side facing away, and a rounded transition from the lower to the upper narrow side can be provided, which in particular includes an acute angle with the upper narrow side bearing the working limb. Consequently, the grip gradually becomes narrower in the anchoring region of the working limb, but has a longer length in the anchoring area, so that there is a sufficiently long overlap between grip and working limb, but nevertheless an excessively sharp edged angle space is avoided at the end of the grips in relation to the working limbs standing opposite thereto.

Overall, there results a bipolar coagulation forceps in which the working limbs are arranged outside of or laterally to the actual grip, whereby at least one of the working limbs can be constructed as a tube for rinsing fluid, and according to need, there is nonetheless space for guidance for the working tips and to be sure in the grip area. Such guidance means are thereby not impeded by a rinsing tube passing along the inside.

BRIEF DESCRIPTION OF THE DRAWINGS

Below embodiments of the invention are described in detail on the basis of the drawings. Depicted are:

FIG. 1 is a side view and

FIG. 2 is a plan view of a bipolar coagulation forceps with a rinsing tube,

FIG. 3 is a cross section taken along the line III—III in FIG. 1,

FIG. 4 is a side view and

FIG. 5 is a plan view of a bipolar coagulation forceps, in which the working limb forming a rinsing tube is replaced by a working limb with a solid section, and FIG. 6 is a cross section of forceps taken along the Line VI—VI in FIG. 4.

DETAILED DESCRIPTION OF PREFERRED EMBODIMENTS

A bipolar coagulation forceps designated as a whole as 1 in both embodiments has a connection 2 for high frequency energy on its end facing away from the working tips 3. It has furthermore two forceps limbs 4 which can be pressed together against spring tension, whose tips 3 opposite the connection 2 for high frequency energy form the poles during coagulation.

In the embodiment in accordance with FIGS. 1–3, it is provided that the forceps limbs 4 consist of grips 5 which can be pressed together against spring tension and working limbs 6 which are subsequently anchored on them, whereby one of these working limbs 6 in accordance with FIG. 3 has a hollow section or is constructed as a tube. One recognizes that this hollow working limb 6 has a connection 7 for rinsing fluid and/or a suction source, so that this coagulation forceps 1 thus possesses a rinsing tube on a forceps limb 4. On the other hand, it emerges from FIG. 3 as well as from FIG. 6 that the working limbs 6 are installed on parallel narrow sides 8 of the grips 5, that is, at the transition between the inner side 9 and the outer side 10 of the respective grip 5.

There consequently results enough space between the grips 5 to provide contact and guidance parts 11 on the inner sides 9 of these grips which face each other, with a distance from the working limbs 6 and the narrow sides 8 bearing these, for restricting and/or guiding the closing path of the working tips 3, as depicted in FIGS. 2 and 5. These contact and guiding parts 11 are not depicted in FIGS. 3 and 6 for the sake of a better overview. By way of example, they correspond to the contact and guidance parts as they are known from DE 31 10 666 C2.

It is hence possible to provide a rinsing tube in the form of a pipe-like working limb 6 with a corresponding connection 7 and nonetheless also accommodate such guidance parts 11 without problems.

In accordance with FIGS. 3 and 6, the cross section of the working limb is circular in the embodiment. The narrow sides 8 of the grips 5 have a groove-like notch or milling, which has an appropriately curved cross section, at least over the length which extends along the working limbs 6 and overlaps with them. In accordance with FIGS. 3 and 6, the curvature of the groove-like notch and the curvature of the outer surface of the working limb 6 match, and the thickness of the grips 5 between their inner side 9 and their outer side 10 corresponds to the diameter of the working limb 6 in question, so that the outer side 10 and the inner side 9 of each grip 5 is flush with the working limb carried by them. The working limbs 6 thus do not stick out from the grips 5, so that the forceps limbs 4 as a whole have a largely constant thickness all the way to the tapering tips, which is advantageous for the task of pressing them together.

One recognizes in FIGS. 1 and 4 that the working limbs 6 only extend over a part of the extent in length of the grips 5, by way of example over about a fourth to a half, preferably over a third of the length of the grips 5, and leave free the remaining longitudinal area of the grips 5 lying nearer to the high frequency connection 2. Weight and effort for the connection between the grip 5 and the working limb 6 can consequently be spared. The overlap only over a fraction of the length of the grip mentioned suffices for firmness.

In the extension of the hollow working limb 6, the rinsing and/or suction connection 7 is anchored on its end facing away from the working tip 3 on the narrow side 8 of the grips. It can be soldered or welded on, but in the embodiment it is a continuation of the working limb 6 in one piece. This provides an especially simple realization of the rinsing tube, which thereby consists of one of the working limbs, on which then merely an appropriate hose connection 12 is to be attached. It thereby becomes clear from observing FIGS. 1 and 2 together that the rinsing connection 7 is installed with its hose connection 12 toward the narrow side 8 of the grip 5 bearing the working limb 6 in the plane arranged at right angles to the closing motion of this grip 5, from one view of the two forceps limbs 4 lying next to each other, thus is practically projected toward one of the forceps limbs 4 or the narrow side. Distance from the real forceps 1 is consequently obtained for the hose which is to be connected, but nevertheless the forceps 1 itself is not enlarged toward the outer sides of the forceps limbs.

Both embodiments show in common that the grips 5 can bear on their narrow sides 8 working limbs 6 with/or without a rinsing connection 7 or with solid section. While in connection with the embodiment according to FIGS. 1 and 2, one working limb 6 has a solid section and the other has a hollow section as a rinsing tube, both working limbs 6 are provided with solid sections in the embodiment according to FIGS. 4 to 6. It thereby becomes clear that identical grips 5 can find application with high frequency energy connections 2 regardless of whether the forceps 1 have a rinsing tube or not, i.e. in connection with the manufacture of such bipolar coagulation forceps, a considerable rationalizing effect can be obtained by an identical use of the grips 5 with the connections 2. This increases the advantage of providing one of the working limbs 6 as a subsequently attached part as a rinsing tube, because manufacturing can occur in the same fashion even with such forceps which lack a rinsing tube.

In addition, one recognizes in the side views in accordance with FIGS. 1 and 4 that the upper narrow side 8 of the grips 5 which bears the working limbs 6 is longer than the turned away lower narrow side 13, and that a rounded transition 14 is hence provided in this case from the lower narrow side 13 to the upper narrow side 8. This transition 14 thus forms an acute angle with the upper narrow side 8 which carries the working limb 6. There consequently arises a largely gradual transition from the relatively broad grips 5 to the basically thinner working limbs 6 mounted on them.

The bipolar coagulation forceps 1 with a connection 2 for high frequency energy and two forceps limbs 4 which can be pressed together against spring tension is so constructed that a rinsing tube can be provided in a simple manner and without impinging on the space between the forceps limbs 4. For this purpose, the forceps limbs 4 comprise grips 5 which can be pressed together against spring tension with working limbs 6 subsequently anchored thereupon, whereby then at least one of the working limbs has a hollow section or is constructed as a tube and has a connection 7 for rinsing fluid, so that guiding parts 11 can be installed between the grips 5 for the mutual guidance of the working tips 3 of the forceps 1. The working limbs 6 are for this reason installed on parallel narrow sides 8 of the grips 5, thus lateral to the grip areas where the guiding parts 11 are accommodated.

I claim:

1. A bipolar coagulation forceps (1) comprising two forceps limbs (4) which can be pressed together against spring tension, the forceps limbs being connected together at a first end and having free ends opposite to the first end, a connection (2) for high frequency energy located at the first end, the forceps limbs (4) including grips (5) having parallel narrow sides and facing inner sides, the grips being capable of being pressed together against the spring tension, and working limbs (6) fastened thereupon which include tips (3) located at the free ends of the forceps limbs which form poles for coagulation, at least one of the working limbs (6) having a closed hollow cross section with the tip of the at least one working limb being formed at the free end of the closed hollow cross section, the closed hollow cross section having a connection (7) for one of a rinsing fluid and a suction source, and the working limbs (6) being fastened on the parallel narrow sides (8) of the grips (5).

2. The coagulation forceps according to claim 1, wherein the cross section of the working limbs (6) is round.

3. The coagulation forceps according to claim 1 wherein the narrow sides (8) have a groove-like notch at least along a length over which the working limbs (6) extend, the groove-like notch having a cross-sectional curvature which corresponds approximately to a curvature on a outer side of the working limb (6).

4. The coagulation forceps according to claim 1 wherein the working limbs (6) extend over about one fourth to about one half of a length of the grips (5), leaving free a remaining longitudinal area of the grips (5) lying closer to the first end with the connection (2) for high frequency energy.

5. The coagulation forceps according to claim 1, wherein the rinsing connection (7) is fastened on an extension of the hollow section at its end facing away from the tips (3).

6. The coagulation forceps according to claim 5, wherein the rinsing connection (7) is formed as one piece with the working limb (6).

7. The coagulation forceps according to claim 5, wherein the rinsing connection (7) is bent away from the narrow side (8) in a plane of the grip (5) oriented at a right angle to a closing movement of the foreceps.

8. The coagulation forceps according to claim 1, wherein a thickness of the grips (5) corresponds approximately to a diameter of a cross section of the working limb (6), and an outer side (10) and an inner side (9) of each grip (5) is largely flush with sides of the working limb (6) borne by them.

9. The coagulation forceps according to claim 1, wherein at least one of the grips (5) carries on its narrow side (8) a working limb (6) with a solid cross section.

10. The coagulation forceps according to claim 1, wherein an upper narrow side (8) of the grips (5) bearing the working limbs (6) is longer than a lower narrow side facing away therefrom, and a rounded transition (14) from the lower narrow side to the upper narrow side (8) is provided which forms an acute angle with the upper narrow side (8).

11. The bipolar coagulation forceps of claim 1 further comprising guidance parts (11) mounted between the grips (5) on the facing inner sides (9) of the grips facing each other, at a distance from the narrow sides (8) bearing the working limbs (6), the guidance parts serving to at least one of restrict and guide a closing path of the tips (3).

12. A bipolar coagulation forceps (1) comprising two forceps limbs (4) which can be pressed together against spring tension, the forceps limbs being connected together at a first end and each forceps limb having a free end opposite to the first end, a connection (2) for high frequency energy located at the first end, the forceps limbs (4) including grips (5) having facing inner sides, the grips being capable of being pressed together against the spring tension, and working limbs (6) fastened to the grips which include tips (3) that comprise the free ends of the forceps limbs, the tips (3) located at the free ends forming poles for coagulation, at least one of the working limbs (6) consisting of a tube having a connection (7) for one of a rinsing fluid and a suction source, the tip of the at least one of the working limbs being formed on the free end of the tube, and guidance parts (11) mounted between the grips (5) on the facing inner sides (9), the guidance parts serving to guide a closing path of the tips (3).

\* \* \* \* \*